US00PP36252P2

(12) United States Plant Patent
Milla-Lewis

(10) Patent No.: US PP36,252 P2
(45) Date of Patent: Nov. 12, 2024

(54) ZOYSIAGRASS PLANT NAMED 'XZ 14069'

(50) Latin Name: ***Zoysia japonica* x *Zoysia matrella***
Varietal Denomination: XZ 14069

(71) Applicant: North Carolina State University, Raleigh, NC (US)

(72) Inventor: Susana Milla-Lewis, Apex, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/445,332

(22) Filed: Jul. 13, 2023

(51) Int. Cl.
*A01H 5/12* (2018.01)
*A01H 6/46* (2018.01)

(52) U.S. Cl.
USPC ..... Plt./390
CPC ..... *A01H 6/469* (2018.05)

(58) Field of Classification Search
USPC ..... Plt./390
CPC ..... A01H 5/12
See application file for complete search history.

(56) References Cited

PUBLICATIONS https://cals.ncsu.edu/crop-and-soil-sciences/news/nc-state-turfgrass-releases-lobo-zoysiagrass/; Nov. 12, 2021; 7 pages.*
https://cdn.ymaws.com/www.ftga.org/resource/resmgr/turf_digest/2020/ftd_fall_2020.pdf; Fall 2020; 5 pages.*
In re Wingen; Feb. 9, 2023; 9 pages.*
Bock , et al., "Plant Disease Severity Estimated Visually, by Digital Photography and Image Analysis, and by Hyperspectral Imaging", Critical Reviews in Plant Sciences, 29(2):59-107, 2010.
Braun , et al., "Performance and playability of experimental low-input coarse-textured zoysiagrass in multiple climates", Grass Research, 1:10, 2021.
Dice, Lee R., "Measures of the Amount of Ecologic Association Between Species", Ecology, 26:297-302, 1945.
Kimball , et al., "Genetic Relationships in *Zoysia* Species and the Identification of Putative Interspecific Hybrids Using Simple Sequence Repeat Markers and Inflorescence Traits", Crop Science, 53:285-295, 2013.
Moore , et al., "SSR Allelic Diversity Shifts in Zoysiagrass (*Zoysia* spp.) Cultivars Released from 1910 to 2016", Crop Science, 57:S-1-S-12, 2017.
Rohlf, James F., "NTSYS-PC: Numerical Taxonomy and Multivariate Analysis System: Getting Started Guide", Department of Ecology and Evolution State University of New York, Version 2.2. Exeter Software, Setauket, NY. (2000) ; 43 pages.
Sokal , et al., "A Statistical Method for Evaluating Systematic Relationships", The University of Kansas Science Bulletin, 28(22): 1409-1438, 1958.

* cited by examiner

*Primary Examiner* — Kent L Bell
(74) *Attorney, Agent, or Firm* — Myers Bigel, P.A.

(57) ABSTRACT

'XZ 14069' is a medium to dark green perennial zoysiagrass cultivar with medium-fine texture low incidence of large patch disease and aggressive stoloniferous growth producing high density turf performance ideal for low-management landscaping. It is distinguishable from other cultivars by medium-fine texture, plant architecture and characteristics such as high drought tolerance, turf quality, disease resistance and aggressive establishment from minimal input. 'XZ 14069' shows persistence under an array of climates including warm-temperate, warm-humid and hot-arid. 'XZ 14069' is also genetically distinct from other zoysiagrass cultivars currently in the marketplace known to the Inventor. 'XZ 14069' exhibits very low fertility and no inflorescences have been observed.

10 Drawing Sheets

Specification includes a Sequence Listing.

STATEMENT OF GOVERNMENT SUPPORT

This invention was made with government support under grant numbers 2015-51181-24291 and 2019-51181-30472 awarded by the USDA National Institute of Food and Agriculture. The government has certain rights in the invention.

Latin name of the genus and species: The Latin name of the novel grass cultivar disclosed herein is *Zoysia japonica* x *Zoysia matrella.*

Variety denomination: The inventive cultivar of *Zoysia japonica* x *Zoysia matrella* disclosed herein has been given the varietal denomination 'XZ 14069'.

STATEMENT REGARDING ELECTRONIC FILING OF A SEQUENCE LISTING

A Sequence Listing in XML format, entitled 5051-1010_ST26.xml, 34,449 bytes in size, generated on Oct. 5, 2023, and filed herewith, is hereby incorporated by reference in its entirety for its disclosures.

BACKGROUND OF THE INVENTION

Zoysiagrasses are warm-season, perennial turfgrass species well-adapted for home lawns, commercial landscapes, and golf courses across the southern US and upwards into the transition zone. Given that zoysiagrasses have lower maintenance requirements than other warm-season grasses, expanded use of this grass could have significant reductions in negative environmental impacts. However, current breeding efforts in the US are focused on fairway and putting green zoysiagrasses. Little effort has been put towards the development of aggressive, vegetatively established zoysiagrass cultivars well-adapted for golf course roughs, lawns, roadsides, airports, and other infrequently mown areas where crop function and stress tolerance are of equal importance to aesthetics. Aggressive zoysiagrass germplasm that has excellent stress tolerance and fast establishment when managed with low to no inputs would increase the prevalence of zoysiagrass use in new markets.

'XZ 14069' is a new zoysiagrass cultivar that is fast to establish, drought tolerant, and able to retain acceptable color and turf quality under very low inputs. Furthermore, this cultivar is not to be limited to low-management situations such as golf course roughs or roadsides, as its above average turf quality makes it suitable to higher end uses like lawns and golf course fairways.

SUMMARY OF THE INVENTION

'XZ 14069' is a perennial zoysiagrass that is spread by stolons and rhizomes and was identified in 2016 because of its turf quality and aggressive growth from a collection of zoysiagrass plants that were evaluated under cultivated conditions in Raleigh, Jacksonville, and Laurel Springs in North Carolina. 'XZ 14069' can be distinguishable from other cultivars by its medium-fine texture, turf quality under low inputs, high density that outcompetes weeds, low seedhead production, aggressive stoloniferous growth during establishment, and low incidence of large patch disease caused by *Rhizoctonia solani* anastomosis group 202 LP. Additionally, Simple Sequence Repeat (SSR) data shows 'XZ 14069' is genetically distinct from all major zoysiagrass cultivars currently on the market known to the Inventor. 'XZ 14069' persists well under an array of climates including warm-temperate, warm-humid and hot-arid, as well as under a range of uses, from low-management situations such as golf course roughs or roadsides to higher-end uses like lawns and golf course fairways.

BRIEF DESCRIPTION OF THE DRAWINGS

The photographs in the drawings were made using conventional techniques and show the colors as true as reasonably possible by conventional photography. Photographs were taken of plant materials grown in greenhouses for eight months. During this period, plants were under daily watering, monthly fertilization, and no mowing. Colors in the photographs may differ slightly from the color values cited in the detailed botanical description, which accurately describe the colors of the new *Zoysia japonica* x *Zoysia matrella* grass 'XZ 14069'.

FIG. 5A is a far view: FIG. 5B is a close view.

FIG. 6 is a data graphic tabulating cumulative turf performance index (TPI) values. The TPI value refers to the number of times a treatment occurred in the top statistical group across all parameters, for all five locations. The maximum possible turf performance index number for each location is as follows: Indiana (13), North Carolina (12), Georgia (7), Arizona (5), and California (4). Treatments with an X indicate the entry or check was not planted at that location.

DETAILED BOTANICAL DESCRIPTION OF THE NEW VARIETY

Figure 1:
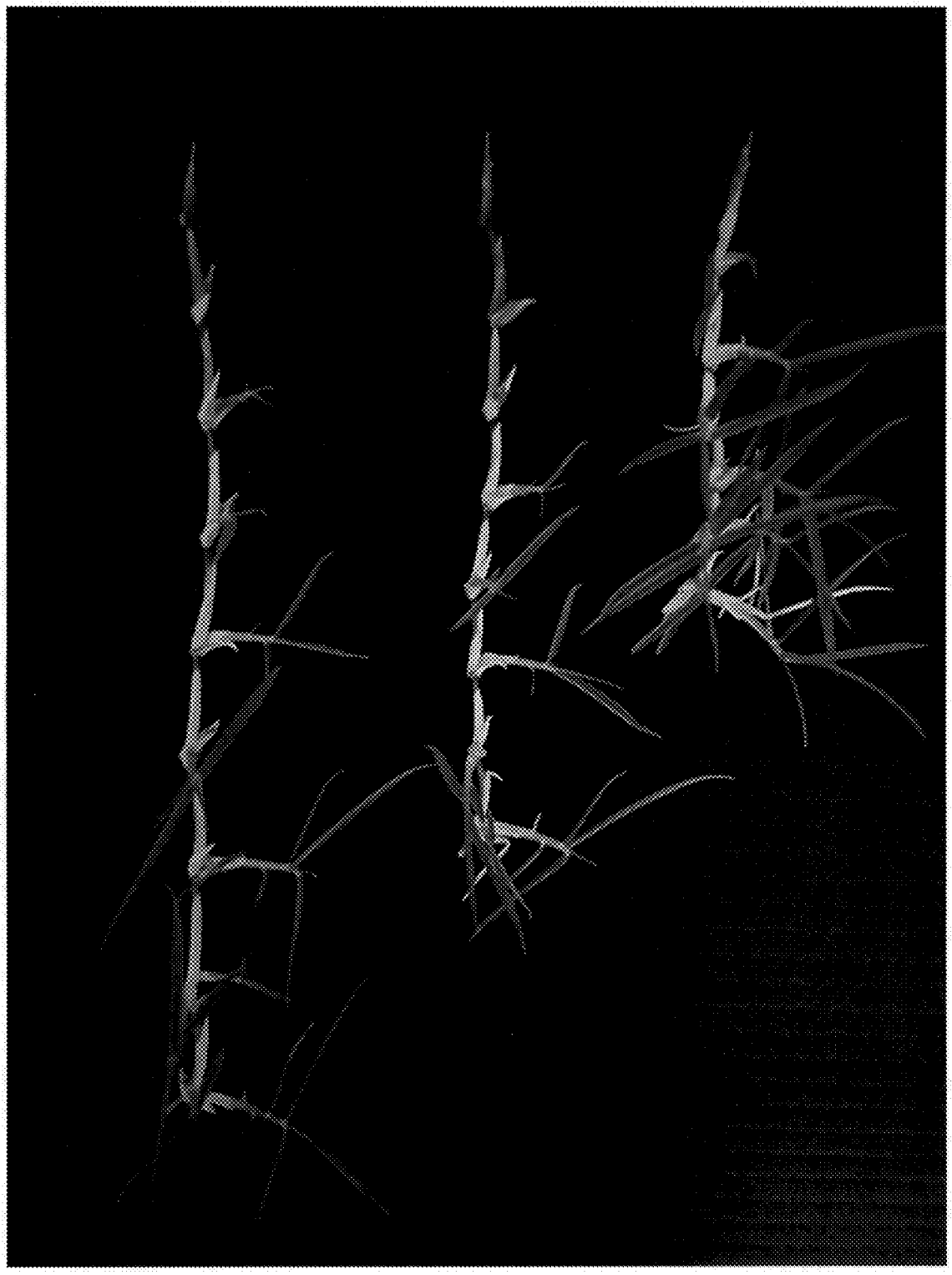
FIG. 1 is a color photograph of stolons of a typical specimen of the claimed plant.

The following is a detailed description of the botanical characteristics of a new and distinct cultivar of *Zoysia* plant known by the cultivar name 'XZ 14069'. All colors cited herein refer to The Royal Horticulture Society (RHS) Colour Chart designations (The Royal Horticultural Society, London, Flower Council of Holland 1986 edition) except where general terms of ordinary dictionary significance are used. Where dimensions, sizes, colors, and other characteristics are given, it is to be understood that such characteristics are approximations or averages set forth as accurately as practicable.

This invention relates to a new and unique cultivar of perennial zoysiagrass plant (*Zoysia japonica* x *Zoysia matrella*) designated as 'XZ 14069'. 'XZ 14069' is an F1 hybrid that was produced in Raleigh, NC in fall 2014 by crossing cultivar 'Meyer' [unpatented *Zoysia japonica* Steud. ] as the female parent with pollen of cultivar 'Victoria' [U.S. Plant Pat. No. 9,135P described therein as *Zoysia matrella* (L.) Merr.; noted as a hybrid *Zoysia japonica* x *Zoysia matrella* per DNA marker analysis as described in Kimball et al. 2013 Crop Science 53(1):285-295]. Crosses of 'Meyer' by 'Victoria' [U.S. Plant Pat. No. 9,135P] were manually made in 2014 under greenhouses conditions. When 'Meyer' inflorescences were ready for pollination, pollen from 'Victoria' [U.S. Plant Pat. No. 9,135P] was collected in petri dishes and pollen grains were spread on the stigmas using a brush. To avoid pollen contamination, stigmas were covered with a glycine shoot bag after pollination (five days). Pollinated flowers reach maturity after four weeks. Harvested seeds were germinated in petri dishes for six weeks. Seedlings were transferred to soil and later to greenhouses where they reached maturity in azalea pots (6 in. diameter×4¼ in. tall). 'XZ 14069' was first vegetatively propagated in Raleigh, NC in 2015 by tillers, rhizomes and stolons, and rooting them in potting soil. Asexually reproduced plants of 'XZ 14069' have remained stable and true to type through at least 7 successive cycles of vegetative propagation. 'XZ 14069' has been determined to be tetraploid (2n=4x=40).

'XZ 14069' has not been observed under all possible environmental conditions: therefore, the phenotype may vary under different environmental conditions such as season, temperature, light intensity, day length, cultural conditions, and the like, without however, any variance in the genotype. The following morphological measurements were collected on 'XZ 14069' plants grown in greenhouse conditions for eight months.

Leaf blades:

*Length.*—21.87 mm.
*Width.*—1.54 mm.
*Shape.*—Keeled.
*Apex.*—Pointed.
*Aspect.*—Concave.
*Margin.*—Smooth.
*Auricle.*—Absent.
*Collar.*—Broad continues with hairy edges.
*Sheath.*—Overlapping.
*Leaf bud.*—Rolled.
*Ligule type.*—Short fringe of hairs.
*Adaxial surface.*—Texture: moderate trichomes. Color: RHS 137A: Green-Group.
*Abaxial surface.*—Texture: smooth. Color: RHS 137B: Green-Group.
*Venation.*—Parallel.

Inflorescence: No inflorescences have been observed under greenhouse conditions since its original development. Under field conditions, data for North Carolina reported 0% seedhead density for both 2020 and 2021 (as tabulated in Tables 1-7 below).

Stolons:

*Internode length.*—11.99 mm.
*Internode color.*—RHS 146C: Yellow-Green-Group.
*Internode diameter.*—1.46 mm Apical meristem.
*Color.*—RHS 146B: Yellow-Green-Group.
*Node diameter.*—2.07 mm.
*Node color.*—RHS 146C: Yellow-Green-Group.

Rhizomes:

*First internode.*—length 7.66mm, width 1.3 mm.
*Second internode.*—length 9.15 mm, width 1.2 mm.
*Third internode.*—length 11.62 mm, width 1.0 mm.
*Node width.*—1.95 mm.
*Internode color.*—RHS 161B: grayed-yellow group.
*Node color.*—RHS 161A: grayed-yellow group.

Plant height average of 'XZ 14069' is 110 mm in pots grown under greenhouse conditions. Plant height under field conditions depends on the standard protocols for mowing set by each sod farm. Data has not been collected.

Figure 2:
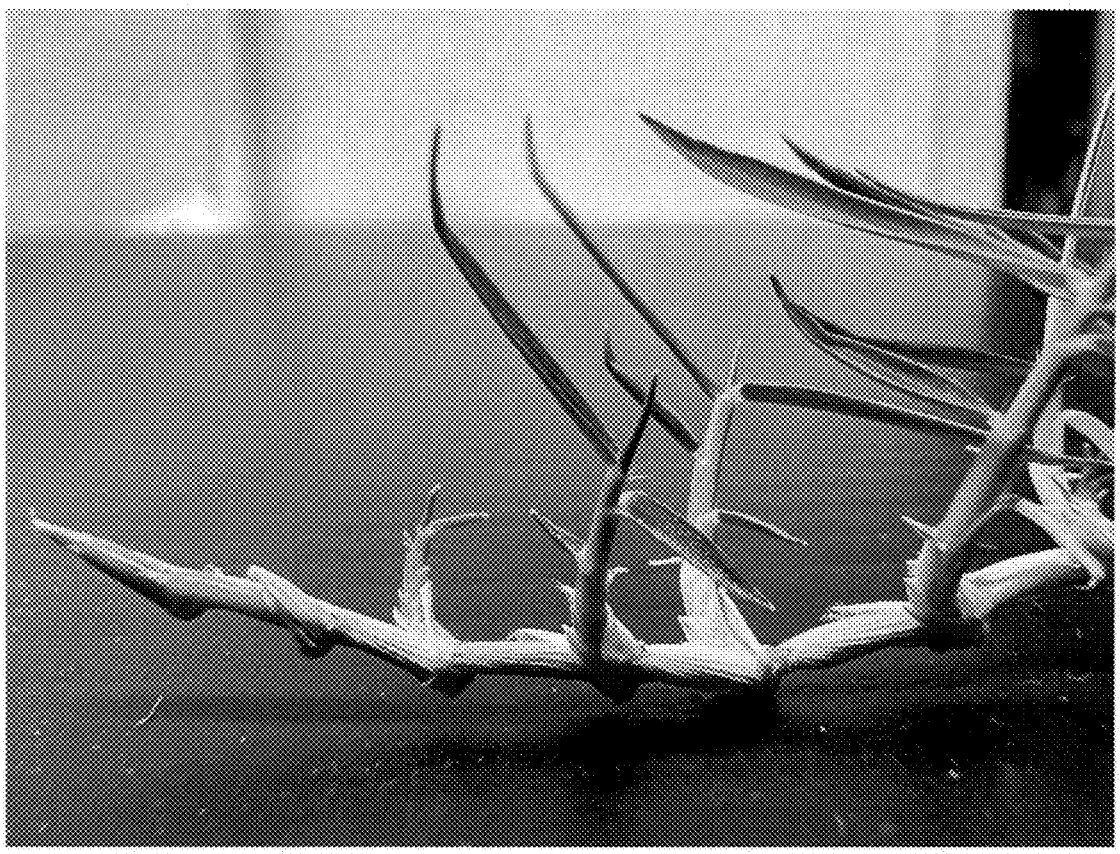
FIG. 2 is a color photograph of a stolon of a typical specimen of the claimed plant.
Figure 3:
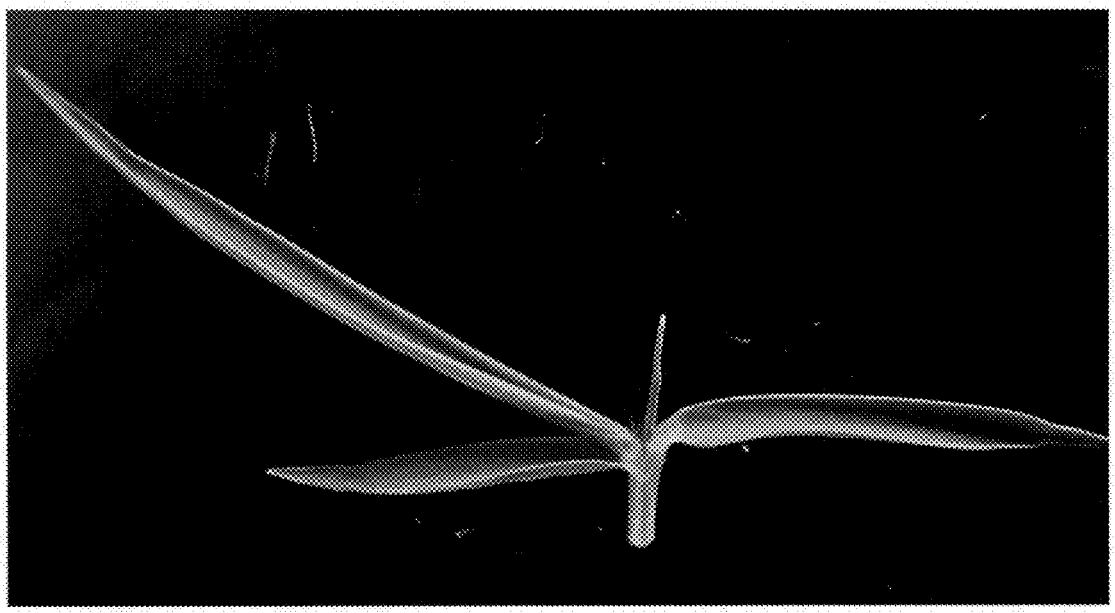
FIG. 3 is a color photograph of leaf blades of a typical specimen of the claimed plant.
Figure 4:
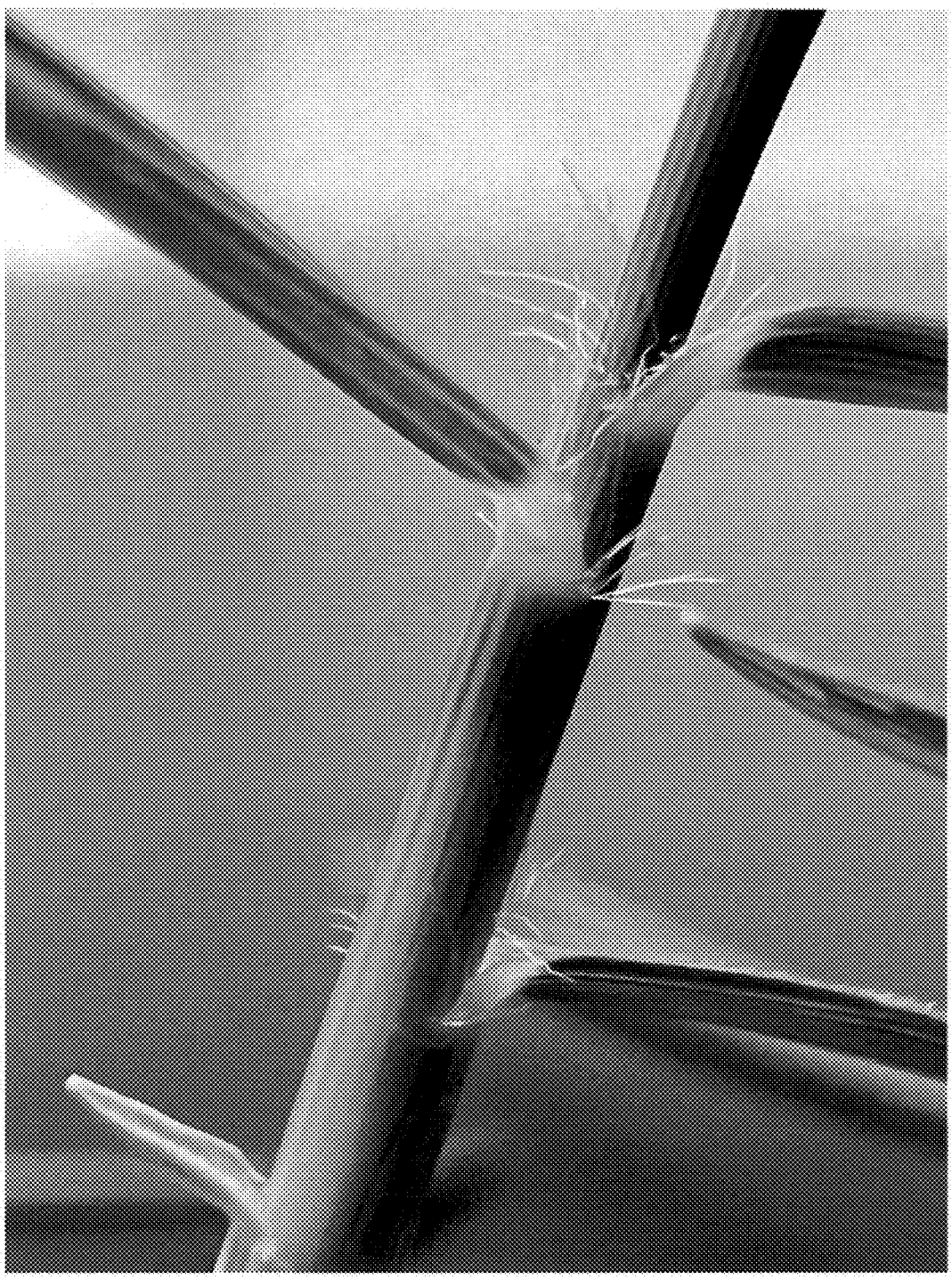
FIG. 4 is a color photograph of leaf hairs of a typical specimen of the claimed plant.
Figure 5A:
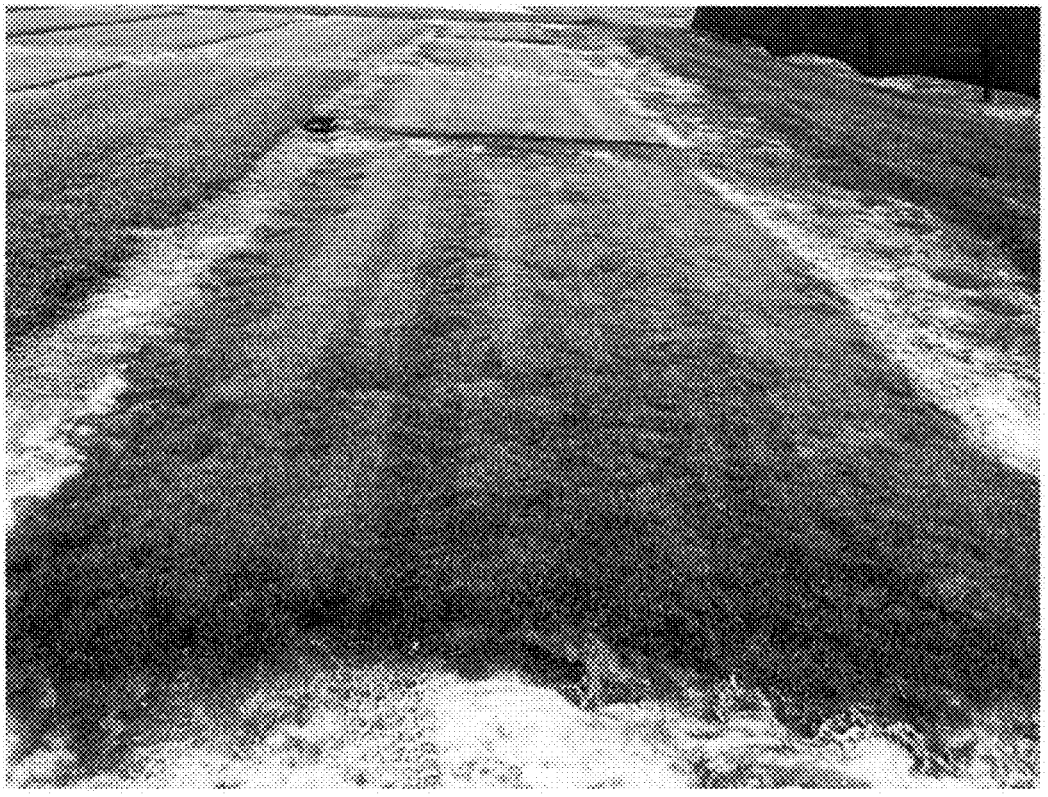
FIGS. 5A-5B are two color photographs of a typical plot of the claimed plant.
Figure 5B:
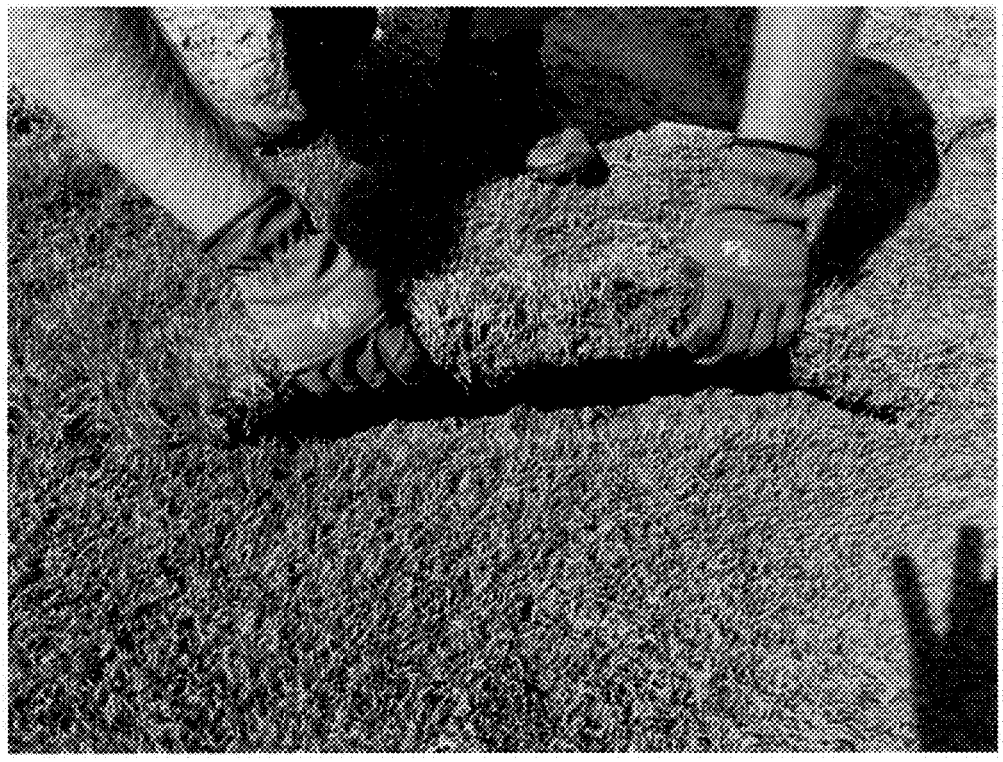

FIGS. 1-5 provide photographic images of the claimed plant. In particular, FIG. 1 shows an example of stolon of a typical specimen of 'XZ 14069'; FIG. 2 shows an example of stolon thickness of a typical specimen of 'XZ 14069'; FIG. 3 shows an example of leaf blades of a typical specimen of 'XZ 14069'; FIG. 4 shows an example of leaf hairs of a typical specimen of 'XZ 14069'; and FIGS. 5A-5B show examples of a plot (FIG. 5A, far view; FIG. 5B, close view) of a typical specimen of 'ZX-14069'.

Morphological analysis of 'XZ 14069' and comparison with other Zoysia cultivars. 'XZ 14069' was morphologically compared to commercial cultivars 'Meyer' (female parent; unpatented), 'Victoria' (male parent: [U.S. Plant Pat. No. 9,135P]), 'El Toro' [U.S. Plant Pat. No. 5,845P], 'Compadre' [unpatented], 'Palisades' [U.S. Plant Pat. No. 11,515P], 'Diamond' [U.S. Plant Pat. No. 10,636P] and 'JaMur' [U.S. Plant Pat. No. 13,178P2]. Analyses were performed in Raleigh, NC, using 8 month old plants. SUN-GRO® HOTICULTURE MM830-F3B 2.8 Cu ft soil enriched with 50-60% sphagnum peat moss, softwood bark, perlite and dolomite limestone was used for propagation. Plant material was propagated into 12.5 cm-diameter by 8.9 cm-deep pots for a total of three pots per entry. Plant materials were established in June 2022 and grown through January 2023 inside a greenhouse. Daily temperatures ranged from 20 to 30° C. Pots were fertilized every 45 days using Turf Builder Southern Lawn Food (32-0-10) from Scotts®. Watering was performed as needed, four to five times per week. Light requirements included natural sunlight only. Pots were left without mowing to trigger stolon development around the pots. In February of 2023, a digital caliper (6 inches precision measuring tool) was used to collect data from morphological traits. Morphological measurements were taken on internode length, internode diameter and node diameter. From each of the three pots per cultivar, nine measurements were collected per trait. Internode diameter and length were measured using the space between the fourth and fifth nodes, while the stolon node diameter was measured at the fourth node. Leaf length and width were collected from the third youngest leaf. In addition, length of the first leaf at the apical meristem was measured separately. 'XZ 14069' did not produce inflorescences. Collected data were analyzed using LSD ($P \leq 0.05$) in R.

Means followed by the same letter are not significantly different at P=0.05.

TABLE 1

Internode length of zoysiagrass commercial cultivars, measured under greenhouses conditions.

| N | Entry | Internode Length (mm) | Group |
|---|---|---|---|
| 1 | 'Compadre' [unpatented] | 30.93 | a |
| 2 | 'Diamond' [U.S. Plant Pat. No. 10,636P] | 8.56 | d |
| 3 | 'El Toro' [U.S. Plant Pat. No. 5,845P] | 19.88 | bc |
| 4 | 'JaMur' [U.S. Plant Pat. No. 13,178P2] | 23.78 | b |
| 5 | 'XZ 14069' | 11.99 | d |
| 6 | 'Meyer' [unpatented] | 16.90 | c |
| 7 | 'Palisades' [U.S. Plant Pat. No. 11,515P] | 16.64 | c |
| 8 | 'Victoria' [U.S. Plant Pat. No. 9,135P] | 11.50 | d |

TABLE 2

Internode diameter of zoysiagrass commercial cultivars, measured under greenhouses conditions.

| N | Entry | Internode Diameter (mm) | Group |
|---|---|---|---|
| 1 | 'Compadre' [unpatented] | 1.45 | b |
| 2 | 'Diamond' [U.S. Plant Pat. No. 10,636P] | 0.67 | d |
| 3 | 'El Toro' [U.S. Plant Pat. No. 5,845P] | 1.77 | a |
| 4 | 'JaMur' [U.S. Plant Pat. No. 13,178P2] | 1.54 | b |
| 5 | 'XZ 14069' | 1.46 | b |
| 6 | 'Meyer' [unpatented] | 1.39 | b |

TABLE 2-continued

Internode diameter of zoysiagrass commercial cultivars, measured under greenhouses conditions.

| N | Entry | Internode Diameter (mm) | Group |
|---|---|---|---|
| 7 | 'Palisades' [U.S. Plant Pat. No. 11,515P] | 1.49 | b |
| 8 | 'Victoria' [U.S. Plant Pat. No. 9,135P] | 1.20 | c |

TABLE 3

Node diameter of zoysiagrass commercial cultivars, measured under greenhouses conditions.

| N | Entry | Node Diameter (mm) | Group |
|---|---|---|---|
| 1 | 'Compadre' [unpatented] | 2.47 | ab |
| 2 | 'Diamond' [U.S. Plant Pat. No. 10,636P] | 1.08 | d |
| 3 | 'El Toro' [U.S. Plant Pat. No. 5,845P] | 2.83 | a |
| 4 | 'JaMur' [U.S. Plant Pat. No. 13,178P2] | 2.35 | b |
| 5 | 'XZ 14069' | 2.07 | bc |
| 6 | 'Meyer' [unpatented] | 2.15 | b |
| 7 | 'Palisades' [U.S. Plant Pat. No. 11,515P] | 2.48 | ab |
| 8 | 'Victoria' [U.S. Plant Pat. No. 9,135P] | 1.69 | c |

TABLE 4

Leaf blade length of zoysiagrass commercial cultivars, measured under greenhouses conditions.

| N | Entry | Leaf Blade Length (mm) | Group |
|---|---|---|---|
| 1 | 'Compadre' [unpatented] | 23.98 | b |
| 2 | 'Diamond' [U.S. Plant Pat. No. 10,636P] | 11.96 | c |
| 3 | 'El Toro' [U.S. Plant Pat. No. 5,845P] | 22.99 | b |
| 4 | 'JaMur' [U.S. Plant Pat. No. 13,178P2] | 32.46 | a |
| 5 | 'XZ 14069' | 21.87 | b |
| 6 | 'Meyer' [unpatented] | 22.85 | b |
| 7 | 'Palisades' [U.S. Plant Pat. No. 11,515P] | 18.92 | b |
| 8 | 'Victoria' [U.S. Plant Pat. No. 9,135P] | 21.54 | b |

TABLE 5

Leaf blade width of zoysiagrass commercial cultivars, measured under greenhouses conditions.

| N | Entry | Leaf Blade Width (mm) | Group |
|---|---|---|---|
| 1 | 'Compadre' [unpatented] | 4.08 | a |
| 2 | 'Diamond' [U.S. Plant Pat. No. 10,636P] | 1.58 | de |

TABLE 5-continued

Leaf blade width of zoysiagrass commercial cultivars, measured under greenhouses conditions.

| N | Entry | Leaf Blade Width (mm) | Group |
|---|---|---|---|
| 3 | 'El Toro' [U.S. Plant Pat. No. 5,845P] | 3.79 | ab |
| 4 | 'JaMur' [U.S. Plant Pat. No. 13,178P2] | 3.72 | b |
| 5 | 'XZ 14069' | 1.54 | e |
| 6 | 'Meyer' [unpatented] | 2.46 | c |
| 7 | 'Palisades' [U.S. Plant Pat. No. 11,515P] | 3.50 | b |
| 8 | 'Victoria' [U.S. Plant Pat. No. 9,135P] | 1.86 | d |

TABLE 6

Leaf sheath length of zoysiagrass commercial cultivars, measured under greenhouses conditions.

| N | Entry | Leaf Sheath Length (mm) | Group |
|---|---|---|---|
| 1 | 'Compadre' [unpatented] | 9.97 | a |
| 2 | 'Diamond' [U.S. Plant Pat. No. 10,636P] | 4.27 | f |
| 3 | 'El Toro' [U.S. Plant Pat. No. 5,845P] | 7.48 | d |
| 4 | 'JaMur' [U.S. Plant Pat. No. 13,178P2] | 9.16 | ab |
| 5 | 'XZ 14069' | 6.18 | e |
| 6 | 'Meyer' [unpatented] | 8.24 | bcd |
| 7 | 'Palisades' [U.S. Plant Pat. No. 11,515P] | 7.69 | cd |
| 8 | 'Victoria' [U.S. Plant Pat. No. 9,135P] | 8.90 | abc |

TABLE 7

First apical leaf length of zoysiagrass commercial cultivars, measured under greenhouses conditions.

| N | Entry | First Apical Leaf Length (mm) | Group |
|---|---|---|---|
| 1 | 'Compadre' [unpatented] | 27.80 | a |
| 2 | 'Diamond' [U.S. Plant Pat. No. 10,636P] | 8.07 | d |
| 3 | 'El Toro' [U.S. Plant Pat. No. 5,845P] | 12.73 | cd |
| 4 | 'JaMur' [U.S. Plant Pat. No. 13,178P2] | 12.79 | cd |
| 5 | 'XZ 14069' | 18.20 | b |
| 6 | 'Meyer' [unpatented] | 16.30 | bc |
| 7 | 'Palisades' [U.S. Plant Pat. No. 11,515P] | 11.42 | cd |
| 8 | 'Victoria' [U.S. Plant Pat. No. 9,135P] | 10.13 | d |

Low-input Trials in Multiple Climates: 24 zoysiagrass lines and commercial cultivars 'Chisholm' [U.S. Plant Pat. No. 30,653P3], 'Meyer' [unpatented], 'Empire' [U.S. Plant Pat. No. 11,466P], 'JaMur' [U.S. Plant Pat. No. 13,178P2], and 'Zenith' [unpatented] were evaluated for performance under low-maintenance regimes across different climates (Table 8).

TABLE 8

Site information for low-input zoysiagrass trials.

| | Indiana | North Carolina | Georgia | Arizona | California |
|---|---|---|---|---|---|
| Location, City | West Lafayette | Raleigh | Tifton | Stanfield | Escondido |
| Latitude and longitude | 40°26' 31"N; 86°55' 47"W | 35°44' 18"N; 78°40' 39"W | 31°28' 30"N; 83°31' 34"W | 32°55' 23"N; 111°56' 17"W | 33°5' 26"N; 117°0' 24"W |
| Soil type | Silt loam | Sandy loam | Loamy sand | Sandy loam | Sandy loam |
| Climate classification[a] | Warm temperate, no dry season, hot summer (Cfa) | Warm temperate, no dry season, hot summer (Cfa) | Warm temperate, no dry season, hot summer (Cfa) | Hot arid, desert, hot summer (BWh) | Arid, steppe, hot dry summer, cool wet winter, (BSk) |
| USDA plant hardiness zone[b] | 5b (−26.1 to −23.3° C.) | 7b (−15 to −12.2° C.) | 8b (−12.2 to −9.4° C.) | 9b (−3.9 to −1.1° C.) | 10a (−1.1 to 1.7° C.) |

[a]From Köppen-Geiger climate map, retrieved from koeppen-geiger.vuwien.ac.at/present.htm.
[b]Average annual extreme minimum temperature in parentheses and USDA plant hardiness zones as defined by USDA.

The colder continental climate for the Indiana site led to greater winterkill during the 2018-2019 winter season. 'XZ 14069' was not bred for cold tolerance and suffered heavy winterkill damage in year one. However, it was able to recover in year two and ranked in the top group of significance for six out of the 13 traits evaluated. In North Carolina, winter injury was generally not as severe as Indiana. 'XZ 14069' was the top ranked line, having a turf performance index (TPI) of 10 out of 12. In Georgia, which represented a warm-humid climate, 'XZ 14069' obtained a TPI of 4 out of 7. In California and Arizona, which represented warm-dry climates, 'XZ 14069' was again one of the top performing lines. Turf performance values for 'XZ 14069' were 5 (out of 5) and 4 (out of 4) for Arizona and California, respectively. When taking into consideration all sites combined, 'XZ 14069' emerges as the line with a highest combined TPI across locations of 29 as compared to 24 for the second highest line (FIG. 6). Furthermore, it was one of only two lines that exhibited stable performance across climates.

'XZ 14069' was submitted to a low-input warm-season species trial which aims at testing performance of entries under reduced fertilization and very limited irrigation. The trial is being evaluated at Jay, FL (FL3); Citra, FL (FL4); Starkville, MS (MS1); Raleigh, NC (NC1): Las Cruces, NM (NM1); Stillwater, OK (OK1); College Station, TX (TX2); and Logan, UT (UT1).

While *Zoysia* species have been found to have fewer major diseases than other turfgrasses, they are very susceptible to large patch, caused by the fungal pathogen *Rhizoctonia solani* Kuhn. Among warm-season turfgrasses, zoysiagrass is one of the most susceptible to the disease. The species often sustain serious damage and recovery can take several weeks or months. Development of cultivars with genetic resistance to the fungus is the most effective means for management of large patch. 'XZ 14069' was evaluated for large patch resistance under controlled environmental conditions at a phytotron in Raleigh, NC. Resistant cultivar 'Diamond' [U.S. Plant Pat. No. 10,636P] was used as a reference as well as cultivars 'Meyer' [unpatented] and 'Zeon' [U.S. Plant Pat. No. 13,166P2]. Plugs of all individuals were grown in Styrofoam cups filled with calcined clay for 2-3 months until fully established. At the time, cups were arranged in a Randomized Complete Block Design with two replications in a walk-in growth chamber at the phytotron. Large patch inoculations were performed by placing 8-R. solani infected rye grain in the crown region of each plant. Plants were kept at 20/18° C. with >75% relative humidity to promote infection. Disease severity was evaluated every three days for 21 days using the Horsfall-Barratt scale (Horsfall and Barratt 1945 *Phytopathology* 35:655; Bock et al. 2010 *Crit Rev in Plant Sciences* 29(2):59-107)). Two runs of inoculations with two reps each were conducted.

TABLE 9

Large patch disease incidence caused by *Rhizoctonia solani* anastomosis group 202 LP.

| N | Entry | Turf Quality (TQ) | groups |
|---|---|---|---|
| 1 | 'Meyer' [unpatented] | 6.5 | a |
| 2 | 'Zeon' [U.S. Plant Pat. No. 13,166P2] | 6.3 | a |
| 3 | 'Diamond' [U.S. Plant Pat. No. 10,636P] | 5 | b |
| 4 | 'XZ 14069' | 5 | b |

DNA Fingerprinting. In order to demonstrate that 'XZ 14069' is a unique genotype and genetically different from all major zoysiagrass cultivars currently on the market known to the Inventor, simple sequence repeat (SSR) markers were used to generate DNA fingerprints of these materials. Thirty-four cultivars (Table 10) and 'XZ 14069' were genotyped with 19 SSR primer pairs (Table 11). A total of 19 loci were amplified (one locus per primer pair). The number of alleles per locus ranged between 3 and 16 for a total of 171 alleles analyzed (Table 11). Levels of polymorphism among the materials analyzed were comparable to those found in previous studies (Kimball et al. 2013 *Crop Science* 53(1): 285-295: Moore et al. 2017 *Crop Science* 57:S-1-S-12). Genetic similarity values were calculated for all pairwise genotype combinations according to Dice (Dice, L. R. 1945 *Ecology* 26: 297-302). Dice similarities were then used to construct a dendrogram using the UPGMA (Sokal and Michener 1958 A statistical method for evaluating systematic relationships. *Univ. Kansas Sci. Bull.* 28: 1409-1438) clustering procedure in order to assess genetic relationships among genotypes. Additionally, a principal coordinate analysis (PCO) was performed for the same purpose.

Figure 7:
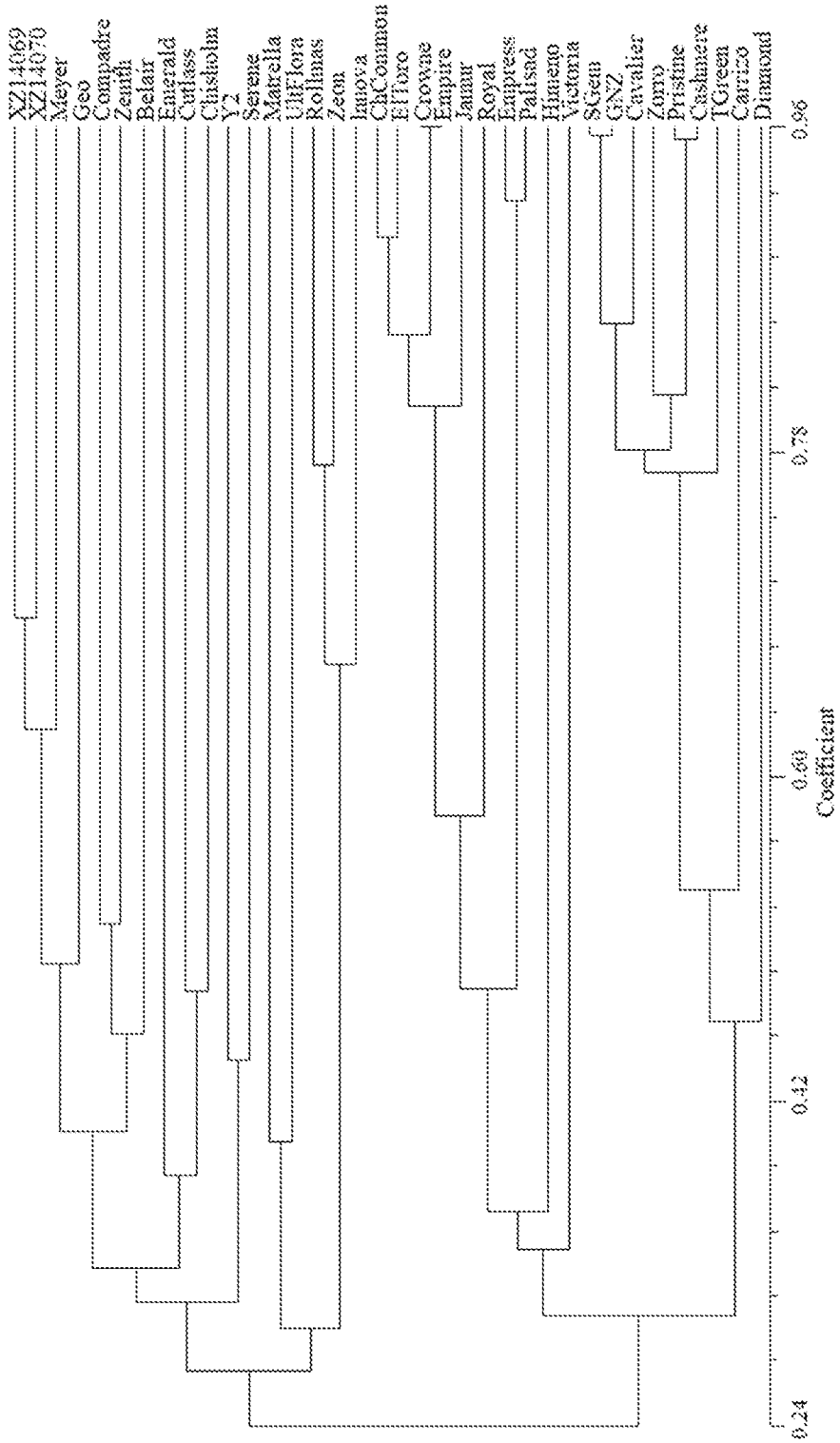
FIG. 7 shows an image of a UPGMA dendrogram of 34 Zoysiagrass commercial cultivars and 'XZ 14069' generated using 171 simple sequence repeat alleles.
Figure 8A:
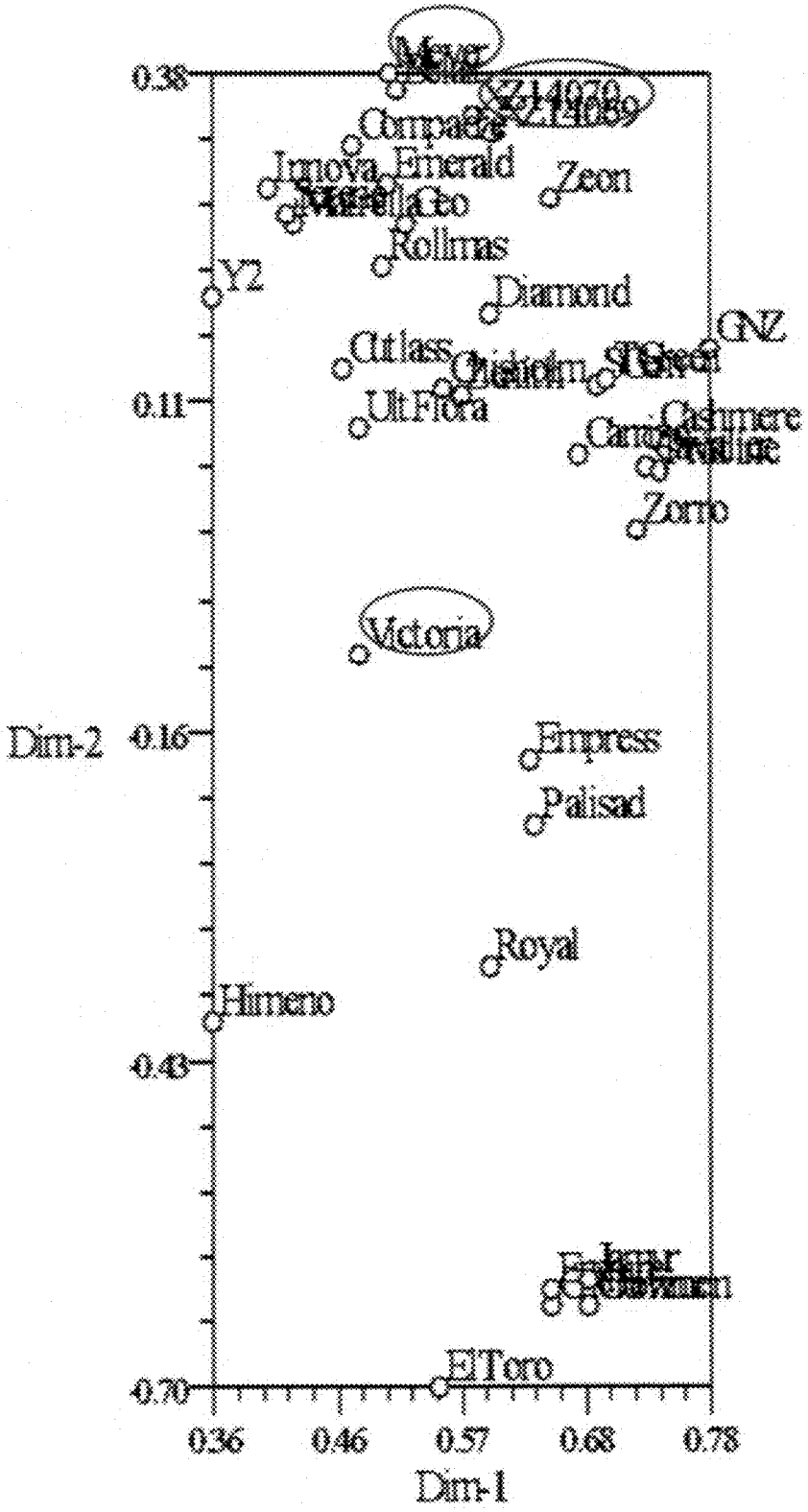
FIGS. 8A-8B show images of Principal Coordinate (PCO) analysis 2D (FIG. 8A) and 3D (FIG. 8B) plots of 32 Zoysiagrass commercial cultivars and 'XZ 14069' generated using 171 simple sequence repeat alleles. 'XZ 14069' and its two parents are circled. 'XZ 14070' is a sister line of 'XZ 14069'.
Figure 8B:
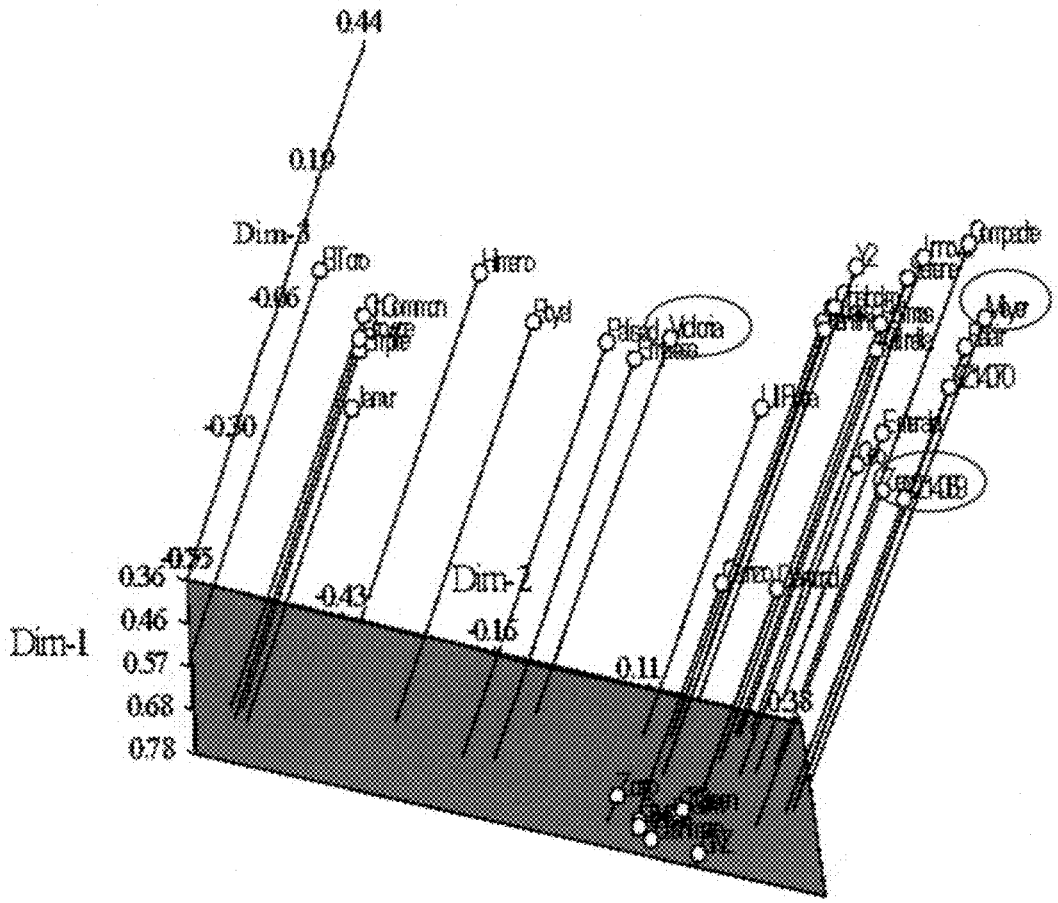
Figure 9:
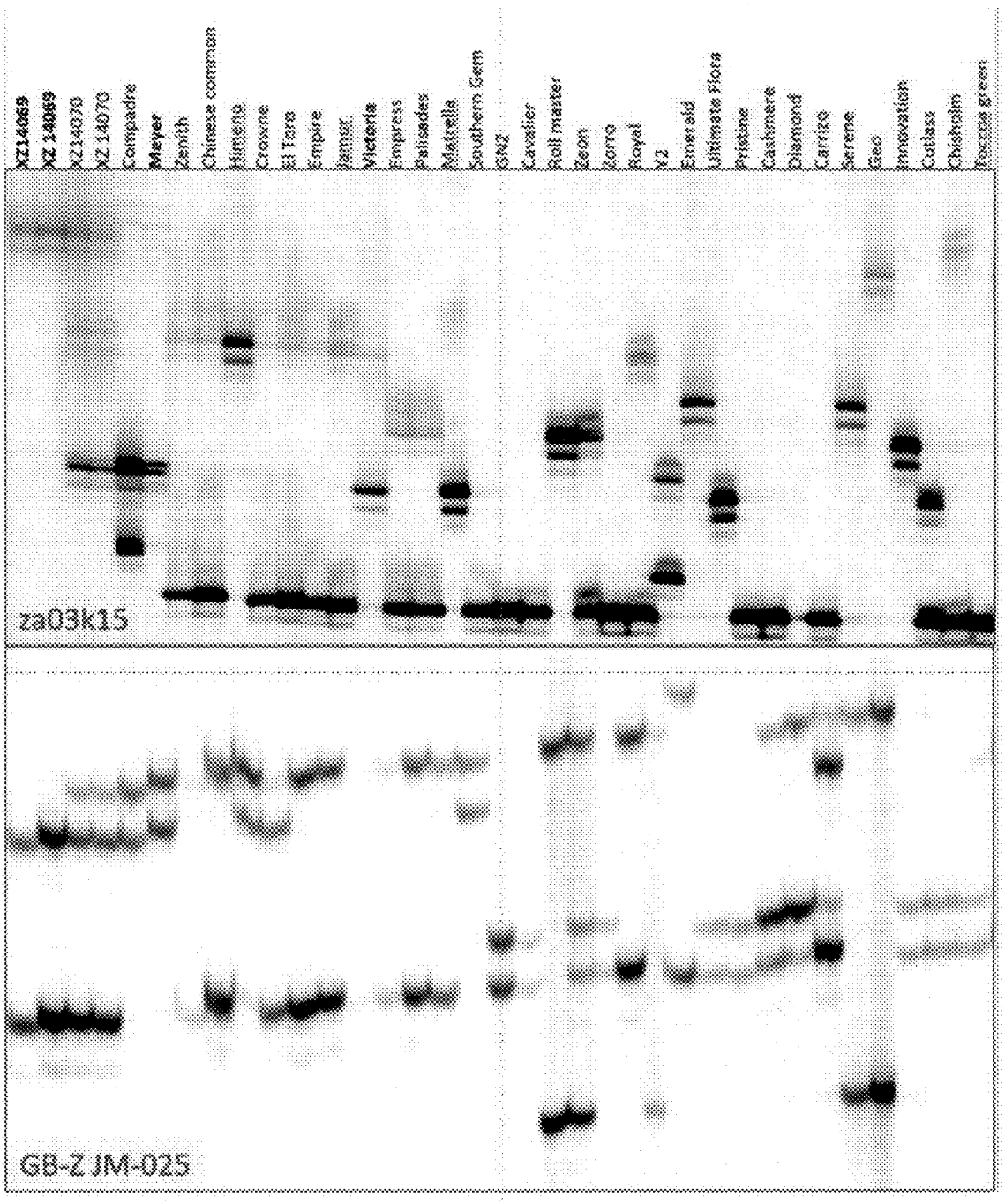
FIG. 9 shows images of PCR amplification of 32 zoysiagrass commercial cultivars and 'XZ 14069' with simple sequence repeat primer pairs za03k 15 and GB-X JM-025 showing unique SSR profiles for 'XZ 14069'.

Genetic similarity values (Sij) for 'XZ 14069' and each of the cultivars tested ranged from 0.13 to 0.60. The average genetic similarity between 'XZ 14069' and each of the other cultivars (Sij= 0.32) is the same as the overall average among all other cultivars (Table 12). 'XZ 14069' is closest to cultivar 'Meyer' (Sij=0.60), one of its parents. However, this distance is sufficiently low to obtain adequate separation among these cultivars as seen in the dendrogram (FIG. 7) and the PCO plots (FIGS. 8A-8B). Only two SSR primers, za03k15 and GB-X JM-025, were sufficient to separate 'XZ 14069' from all other cultivars tested (FIG. 9). The SSR data presented here provides further evidence that 'XZ 14069' is a unique genotype.

TABLE 10

List of genotypes used for comparison of genetic similarity between 'XZ 14069' and major commercial cultivars of zoysiagrass.

| Number | Genotype | Species Designation | Confirmed Species Designation* |
|---|---|---|---|
| 1 | 'XZ 14069' | *Z. japonica x Z. matrella* | — |
| 2 | 'Belair' [unpatented] | *Zoysia japonica* | *Z. japonica* |
| 3 | 'Carrizo' [U.S. Plant Pat. No. 17,808] | *Zoysia japonica* | — |
| 4 | 'Cashmere' [U.S. Plant Pat. No. 6,529] | *Zoysia matrella* | *Z. matrella* |
| 5 | 'Cavalier' [U.S. Plant Pat. No. 10,778P] | *Zoysia matrella* | *Z. japonica x Z. matrella* |
| 6 | 'Chinese Common' [unpatented] | *Zoysia japonica* | *Z. japonica* |
| 7 | 'Chisholm' [U.S. Plant Pat. No. 30,653P3] | *Zoysia japonica* | — |
| 8 | 'Compadre' [unpatented] | *Zoysia japonica* | *Z. japonica* |
| 9 | 'Crowne' [U.S. Plant Pat. No. 11,570] | *Zoysia japonica* | *Z. japonica x Z. matrella* |
| 10 | 'Cutlass' [U.S. Plant Pat. No. 25,380] | *Zoysia japonica* | — |
| 11 | 'Diamond' [U.S. Plant Pat. No. 10,636P] | *Zoysia matrella* | *Z. matrella* |
| 12 | 'El Toro' [U.S. Plant Pat. No. 5,845P] | *Zoysia japonica* | *Z. japonica x Z. matrella* |
| 13 | 'Emerald' [unpatented] | *Z. japonica x Z. pacifica* | *Z. japonica x Z. matrella* |
| 14 | 'Empire' [U.S. Plant Pat. No. 11,466] | *Zoysia japonica* | *Z. japonica x Z. matrella* |
| 15 | 'Empress' [U.S. Plant Pat. No. 11,495] | *Zoysia japonica* | *Z. japonica x Z. matrella* |
| 16 | 'Geo' [U.S. Plant Pat. No. 27,051P3] | *Z. japonica x Z. pacifica* | — |
| 17 | 'GNZ' [U.S. Plant Pat. No. 7,074] | *Zoysia japonica* | *Z. japonica x Z. matrella* |
| 18 | 'Himeno' [U.S. Plant Pat. No. 13,267P3] | *Zoysia japonica* | *Z. japonica* |

TABLE 10-continued

List of genotypes used for comparison of genetic similarity between 'XZ 14069' and major commercial cultivars of zoysiagrass.

| Number | Genotype | Species Designation | Confirmed Species Designation* |
|---|---|---|---|
| 19 | 'Innovation' [U.S. Plant Pat. No. 31,464P3] | *Zoysia japonica* | — |
| 20 | 'JaMur' [U.S. Plant Pat. No. 13,178P2] | *Zoysia japonica* | *Z. japonica x Z. matrella* |
| 21 | 'Matrella' [unpatented] | *Zoysia matrella* | *Z. japonica x Z. matrella* |
| 22 | 'Meyer' [unpatented] | *Zoysia japonica* | *Z. japonica* |
| 23 | 'Palisades' [U.S. Plant Pat. No. 11,515P] | *Zoysia japonica* | *Z. japonica x Z. matrella* |
| 24 | 'Pristine' [U.S. Plant Pat. No. 18,415P3] | *Zoysia matrella* | *Z. matrella* |
| 25 | 'Rollmaster' [unpatented] | *Zoysia matrella* | *Z. japonica x Z. matrella* |
| 26 | 'Royal' [U.S. Plant Pat. No. 14,395] | *Z. japonica x Z. matrella* | *Z. japonica x Z. matrella* |
| 27 | 'Serene' [U.S. Plant Pat. No. 14,175P2] | *Zoysia japonica* | *Z. japonica x Z. matrella* |
| 28 | 'Southern Gem' [U.S. Plant Pat. No. 15,218P2] | *Zoysia japonica* | *Z. japonica x Z. matrella* |
| 29 | 'Toccoa Green' [U.S. Plant Pat. No. 18,405] | *Z. japonica x Z. pacifica* | *Z. matrella* |
| 30 | 'Ultimate Flora' [U.S. Plant Pat. No. 23,716P3] | *Zoysia matrella* | *Z. matrella* |
| 31 | 'Victoria' [U.S. Plant Pat. No. 9,135P] | *Zoysia japonica* | *Z. japonica x Z. matrella* |
| 32 | 'Y2' [U.S. Plant Pat. No. 17,824P2] | *Zoysia japonica* | *Z. japonica x Z. matrella* |
| 33 | 'Zenith' [unpatented] | *Zoysia japonica* | *Z. japonica* |
| 34 | 'Zeon' [U.S. Plant Pat. No. 13,166P2] | *Zoysia matrella* | *Z. japonica x Z. matrella* |
| 35 | 'Zorro' [U.S. Plant Pat. No. 14,130] | *Zoysia matrella* | *Z. japonica x Z. matrella* |

*As determined by simple sequence repeat (SSR) analysis in Kimball et al. (2013)

TABLE 11

Summary statistics for simple sequence repeat (SSR) primers used to assess genetic relatedness among 'XZ 14069' and 34 zoysiagrass commercial cultivars.

| Primer Pair No. | Primer Name | Forward | SEQ ID NO: | Reverse | SEQ ID NO: | No. of alleles amplified |
|---|---|---|---|---|---|---|
| 1 | za01p11 | CACGACGTTGTAAAACGACTCCGCTACCAAGTAATCACT | 1 | TGCGCTTTCTAGAGATCTTC | 2 | 14 |
| 2 | za03k14 | CACGACGTTGTAAAACGACAGGACCAGTGAACATAGTGG | 3 | TGATTGAACAGAAAATTCACC | 4 | 12 |
| 3 | a02o06 | CACGACGTTGTAAAACGACGATTGAAGCTCATGTCTATGTG | 5 | GCAATAAACAACTCTCTTCCTC | 6 | 5 |
| 4 | b02c06 | CACGACGTTGTAAAACGACCAGTTGCTGCTAAGGATTCT | 7 | CCTCGCTATGAGTGGTCTAC | 8 | 7 |
| 5 | b02g05 | CACGACGTTGTAAAACGACGGAGCATATATGGATGCATT | 9 | ACCTGAGGAGGACCAGAG | 10 | 13 |
| 6 | b03g12 | CACGACGTTGTAAAACGACGTTCACAGTTCAAGAAAGCC | 11 | TTGCTCTCACTCCAAAGGA | 12 | 16 |

TABLE 11-continued

Summary statistics for simple sequence repeat (SSR) primers used to assess genetic relatedness among 'XZ 14069' and 34 zoysiagrass commercial cultivars.

| Primer Pair No. | Primer Name | Forward | SEQ ID NO: | Reverse | SEQ ID NO: | No. of alleles amplified |
|---|---|---|---|---|---|---|
| 7 | b06j18 | CAAATGAGCGTCCA TTTC | 13 | GTTGATGCCAC AGACAAAG | 14 | 11 |
| 8 | b07i05 | CACGACGTTGTAAA ACGACATGGAATTA ATCTTCTCCCTG | 15 | GTTGCCTCTTT CATACTTGTG | 16 | 10 |
| 9 | b01b12 | GCTAGTGTTTGTTGA TGACTTG | 17 | AACTTGAGCGT GCTATGC | 18 | 7 |
| 10 | zb01b13 | GCATATCAGTGAAA AGGAGC | 19 | TTATGCTCGCA CAAGAGTC | 20 | 6 |
| 11 | zb01c23a | CAAGAGGAGTTTGG GCTC | 21 | TCAGTCCCTCA AGGAAATTA | 22 | 9 |
| 12 | zb01d04 | AGTAGTGTTTGGAA TCTTCCG | 23 | ACAGTAGCTTG TTTCCTCTCTG | 24 | 15 |
| 13 | GB-ZJM-025 | AGGTCGGAGATGGA GAGC | 25 | CCCGCCTCATG ATAAATG | 26 | 6 |
| 14 | GB-ZJM-051 | GCTTGCAGGATAAG GGGA | 27 | CATGCATAAAT GTGGGGG | 28 | 6 |
| 15 | GB-ZJM-136 | CGTTGATATCGAAC CGGA | 29 | ACCGTCGAGC ACTAGCAA | 30 | 3 |
| 16 | a01a07 | ATTCCTGATCATCTG AGACTTC | 31 | AATTACTGCCA TTTCTGGC | 32 | 9 |
| 17 | a03f03 | ATCAAGGTAACAAG ATCACGA | 33 | GAGAAGGACG TAACGTAACAA | 34 | 7 |
| 18 | b01c16 | AGGACAAGTGAGGC AGTAGA | 35 | AAAGGTCAGTC TCCGTCC | 36 | 9 |
| 19 | b08k21 | GAGAACGACGTCCT GGAC | 37 | ACTTCGCACAC AGAGAAGAC | 38 | 6 |
| Total | | | | | | 171 |
| Average | | | | | | 9.00 |
| Min | | | | | | 3 |
| Max | | | | | | 16 |

TABLE 12

Dice genetic similarities among 'XZ 14069' and 34 selected zoysiagrass commercial cultivars estimated with 19 SSR primer pairs.

| | 'XZ 14069' |
|---|---|
| 'Compadre' [unpatented] | 0.39 |
| 'Meyer' [unpatented] | 0.60 |
| 'Zenith' [unpatented] | 0.40 |
| 'Chinese Common' [unpatented] | 0.20 |
| 'Himeno' [U.S. Plant Pat. No. 13,267P3] | 0.15 |
| 'Crowne' [U.S. Plant Pat. No. 11,570] | 0.26 |
| 'El Toro' [U.S. Plant Pat. No. 5,845P] | 0.13 |
| 'Empire' [U.S. Plant Pat. No. 11,466P] | 0.24 |
| 'JaMur' [U.S. Plant Pat. No. 13,178P2] | 0.23 |
| 'Victoria' [U.S. Plant Pat. No. 9,135P] | 0.19 |
| 'Empress' [U.S. Plant Pat. No. 11,495] | 0.31 |
| 'Palisades' [U.S. Plant Pat. No. 11,515P] | 0.30 |
| 'Matrella' [unpatented] | 0.32 |
| 'Southern Gem' [U.S. Plant Pat. No. 15,218P2] | 0.36 |
| 'GNZ' [U.S. Plant Pat. No. 7,074] | 0.55 |
| 'Cavalier' [U.S. Plant Pat. No. 10,778P] | 0.42 |

TABLE 12-continued

Dice genetic similarities among 'XZ 14069' and 34 selected zoysiagrass commercial cultivars estimated with 19 SSR primer pairs.

| | 'XZ 14069' |
|---|---|
| 'Rollmaster' [unpatented] | 0.27 |
| 'Zeon' [U.S. Plant Pat. No. 13,166P2] | 0.35 |
| 'Zorro' [U.S. Plant Pat. No. 14,130] | 0.40 |
| 'Royal' [U.S. Plant Pat. No. 14,395] | 0.25 |
| 'Y2' [U.S. Plant Pat. No. 17,824P2] | 0.25 |
| 'Emerald' [unpatented] | 0.42 |
| 'Ultimate Flora' [U.S. Plant Pat. No. 23,716P3] | 0.25 |
| 'Pristine' [U.S. Plant Pat. No. 18,415P3] | 0.36 |
| 'Cashmere' [U.S. Plant Pat. No. 6,529] | 0.38 |
| 'Diamond' [U.S. Plant Pat. No. 10,636P] | 0.36 |
| 'Carrizo' [U.S. Plant Pat. No. 17,808] | 0.33 |
| 'Serene' [U.S. Plant Pat. No. 14,175P2] | 0.29 |
| 'Geo' [U.S. Plant Pat. No. 27,051P3] | 0.57 |

TABLE 12-continued

Dice genetic similarities among 'XZ 14069' and 34 selected zoysiagrass commercial cultivars estimated with 19 SSR primer pairs.

| | 'XZ 14069' |
|---|---|
| 'Innovation' [U.S. Plant Pat. No. 31,464P3] | 0.18 |
| 'Cutlass' [U.S. Plant Pat. No. 25,380] | 0.24 |
| 'Chisholm' [U.S. Plant Pat. No. 30,653P3] | 0.28 |

TABLE 12-continued

Dice genetic similarities among 'XZ 14069' and 34 selected zoysiagrass commercial cultivars estimated with 19 SSR primer pairs.

| | 'XZ 14069' |
|---|---|
| 'Belair' [unpatented] | 0.32 |
| 'Toccoa Green' [U.S. Plant Pat. No. 18,405] | 0.42 |

SEQUENCE LISTING

```
Sequence total quantity: 38
SEQ ID NO: 1            moltype = DNA  length = 39
FEATURE                 Location/Qualifiers
source                  1..39
                        mol_type = other DNA
                        organism = synthetic construct
SEQUENCE: 1
cacgacgttg taaaacgact ccgctaccaa gtaatcact                          39

SEQ ID NO: 2            moltype = DNA  length = 20
FEATURE                 Location/Qualifiers
source                  1..20
                        mol_type = other DNA
                        organism = synthetic construct
SEQUENCE: 2
tgcgctttct agagatcttc                                               20

SEQ ID NO: 3            moltype = DNA  length = 39
FEATURE                 Location/Qualifiers
source                  1..39
                        mol_type = other DNA
                        organism = synthetic construct
SEQUENCE: 3
cacgacgttg taaaacgaca ggaccagtga acatagtgg                          39

SEQ ID NO: 4            moltype = DNA  length = 21
FEATURE                 Location/Qualifiers
source                  1..21
                        mol_type = other DNA
                        organism = synthetic construct
SEQUENCE: 4
tgattgaaca gaaaattcac c                                             21

SEQ ID NO: 5            moltype = DNA  length = 41
FEATURE                 Location/Qualifiers
source                  1..41
                        mol_type = other DNA
                        organism = synthetic construct
SEQUENCE: 5
cacgacgttg taaaacgacg attgaagctc atgtctatgt g                       41

SEQ ID NO: 6            moltype = DNA  length = 22
FEATURE                 Location/Qualifiers
source                  1..22
                        mol_type = other DNA
                        organism = synthetic construct
SEQUENCE: 6
gcaataaaca actctcttcc tc                                            22

SEQ ID NO: 7            moltype = DNA  length = 39
FEATURE                 Location/Qualifiers
source                  1..39
                        mol_type = other DNA
                        organism = synthetic construct
SEQUENCE: 7
cacgacgttg taaaacgacc agttgctgct aaggattct                          39

SEQ ID NO: 8            moltype = DNA  length = 20
FEATURE                 Location/Qualifiers
source                  1..20
                        mol_type = other DNA
                        organism = synthetic construct
SEQUENCE: 8
cctcgctatg agtggtctac                                               20
```

-continued

```
SEQ ID NO: 9            moltype = DNA  length = 39
FEATURE                 Location/Qualifiers
source                  1..39
                        mol_type = other DNA
                        organism = synthetic construct
SEQUENCE: 9
cacgacgttg taaaacgacg gagcatatat ggatgcatt                          39

SEQ ID NO: 10           moltype = DNA  length = 18
FEATURE                 Location/Qualifiers
source                  1..18
                        mol_type = other DNA
                        organism = synthetic construct
SEQUENCE: 10
acctgaggag gaccagag                                                 18

SEQ ID NO: 11           moltype = DNA  length = 39
FEATURE                 Location/Qualifiers
source                  1..39
                        mol_type = other DNA
                        organism = synthetic construct
SEQUENCE: 11
cacgacgttg taaaacgacg ttcacagttc aagaaagcc                          39

SEQ ID NO: 12           moltype = DNA  length = 19
FEATURE                 Location/Qualifiers
source                  1..19
                        mol_type = other DNA
                        organism = synthetic construct
SEQUENCE: 12
ttgctctcac tccaaagga                                                19

SEQ ID NO: 13           moltype = DNA  length = 18
FEATURE                 Location/Qualifiers
source                  1..18
                        mol_type = other DNA
                        organism = synthetic construct
SEQUENCE: 13
caaatgagcg tccatttc                                                 18

SEQ ID NO: 14           moltype = DNA  length = 19
FEATURE                 Location/Qualifiers
source                  1..19
                        mol_type = other DNA
                        organism = synthetic construct
SEQUENCE: 14
gttgatgcca cagacaaag                                                19

SEQ ID NO: 15           moltype = DNA  length = 40
FEATURE                 Location/Qualifiers
source                  1..40
                        mol_type = other DNA
                        organism = synthetic construct
SEQUENCE: 15
cacgacgttg taaaacgaca tggaattaat cttctccctg                         40

SEQ ID NO: 16           moltype = DNA  length = 21
FEATURE                 Location/Qualifiers
source                  1..21
                        mol_type = other DNA
                        organism = synthetic construct
SEQUENCE: 16
gttgcctctt tcatacttgt g                                             21

SEQ ID NO: 17           moltype = DNA  length = 22
FEATURE                 Location/Qualifiers
source                  1..22
                        mol_type = other DNA
                        organism = synthetic construct
SEQUENCE: 17
gctagtgttt gttgatgact tg                                            22

SEQ ID NO: 18           moltype = DNA  length = 18
FEATURE                 Location/Qualifiers
source                  1..18
                        mol_type = other DNA
                        organism = synthetic construct
```

-continued

```
SEQUENCE: 18
aacttgagcg tgctatgc                                                  18

SEQ ID NO: 19          moltype = DNA  length = 20
FEATURE                Location/Qualifiers
source                 1..20
                       mol_type = other DNA
                       organism = synthetic construct
SEQUENCE: 19
gcatatcagt gaaaaggagc                                                20

SEQ ID NO: 20          moltype = DNA  length = 19
FEATURE                Location/Qualifiers
source                 1..19
                       mol_type = other DNA
                       organism = synthetic construct
SEQUENCE: 20
ttatgctcgc acaagagtc                                                 19

SEQ ID NO: 21          moltype = DNA  length = 18
FEATURE                Location/Qualifiers
source                 1..18
                       mol_type = other DNA
                       organism = synthetic construct
SEQUENCE: 21
caagaggagt ttgggctc                                                  18

SEQ ID NO: 22          moltype = DNA  length = 20
FEATURE                Location/Qualifiers
source                 1..20
                       mol_type = other DNA
                       organism = synthetic construct
SEQUENCE: 22
tcagtccctc aaggaaatta                                                20

SEQ ID NO: 23          moltype = DNA  length = 21
FEATURE                Location/Qualifiers
source                 1..21
                       mol_type = other DNA
                       organism = synthetic construct
SEQUENCE: 23
agtagtgttt ggaatcttcc g                                              21

SEQ ID NO: 24          moltype = DNA  length = 22
FEATURE                Location/Qualifiers
source                 1..22
                       mol_type = other DNA
                       organism = synthetic construct
SEQUENCE: 24
acagtagctt gtttcctctc tg                                             22

SEQ ID NO: 25          moltype = DNA  length = 18
FEATURE                Location/Qualifiers
source                 1..18
                       mol_type = other DNA
                       organism = synthetic construct
SEQUENCE: 25
aggtcggaga tggagagc                                                  18

SEQ ID NO: 26          moltype = DNA  length = 18
FEATURE                Location/Qualifiers
source                 1..18
                       mol_type = other DNA
                       organism = synthetic construct
SEQUENCE: 26
cccgcctcat gataaatg                                                  18

SEQ ID NO: 27          moltype = DNA  length = 18
FEATURE                Location/Qualifiers
source                 1..18
                       mol_type = other DNA
                       organism = synthetic construct
SEQUENCE: 27
gcttgcagga taagggga                                                  18

SEQ ID NO: 28          moltype = DNA  length = 18
FEATURE                Location/Qualifiers
source                 1..18
```

-continued

```
                        mol_type = other DNA
                        organism = synthetic construct
SEQUENCE: 28
catgcataaa tgtggggg                                                  18

SEQ ID NO: 29           moltype = DNA  length = 18
FEATURE                 Location/Qualifiers
source                  1..18
                        mol_type = other DNA
                        organism = synthetic construct
SEQUENCE: 29
cgttgatatc gaaccgga                                                  18

SEQ ID NO: 30           moltype = DNA  length = 18
FEATURE                 Location/Qualifiers
source                  1..18
                        mol_type = other DNA
                        organism = synthetic construct
SEQUENCE: 30
accgtcgagc actagcaa                                                  18

SEQ ID NO: 31           moltype = DNA  length = 22
FEATURE                 Location/Qualifiers
source                  1..22
                        mol_type = other DNA
                        organism = synthetic construct
SEQUENCE: 31
attcctgatc atctgagact tc                                             22

SEQ ID NO: 32           moltype = DNA  length = 19
FEATURE                 Location/Qualifiers
source                  1..19
                        mol_type = other DNA
                        organism = synthetic construct
SEQUENCE: 32
aattactgcc atttctggc                                                 19

SEQ ID NO: 33           moltype = DNA  length = 21
FEATURE                 Location/Qualifiers
source                  1..21
                        mol_type = other DNA
                        organism = synthetic construct
SEQUENCE: 33
atcaaggtaa caagatcacg a                                              21

SEQ ID NO: 34           moltype = DNA  length = 21
FEATURE                 Location/Qualifiers
source                  1..21
                        mol_type = other DNA
                        organism = synthetic construct
SEQUENCE: 34
gagaaggacg taacgtaaca a                                              21

SEQ ID NO: 35           moltype = DNA  length = 20
FEATURE                 Location/Qualifiers
source                  1..20
                        mol_type = other DNA
                        organism = synthetic construct
SEQUENCE: 35
aggacaagtg aggcagtaga                                                20

SEQ ID NO: 36           moltype = DNA  length = 18
FEATURE                 Location/Qualifiers
source                  1..18
                        mol_type = other DNA
                        organism = synthetic construct
SEQUENCE: 36
aaaggtcagt ctccgtcc                                                  18

SEQ ID NO: 37           moltype = DNA  length = 18
FEATURE                 Location/Qualifiers
source                  1..18
                        mol_type = other DNA
                        organism = synthetic construct
SEQUENCE: 37
gagaacgacg tcctggac                                                  18

SEQ ID NO: 38           moltype = DNA  length = 20
```

-continued

```
FEATURE                 Location/Qualifiers
source                  1..20
                        mol_type = other DNA
                        organism = synthetic construct
SEQUENCE: 38
acttcgcaca cagagaagac                                          20
```

I claim:

1. A new and distinct cultivar of *Zoysia* plant named 'XZ 14069', substantially as illustrated and described herein.

* * * * *

FIG. 6

TURF PERFORMANCE INDEX

| | IN | NC | GA | AZ | CA |
|---|---|---|---|---|---|
| PURZ 1602 | 6 | 3 | 0 | 0 | 0 |
| PURZ 1603 | 3 | 3 | 0 | 0 | 0 |
| PURZ 1606 | 5 | 4 | 1 | 0 | 0 |
| PURZ 1701 | 8 | 3 | 0 | 0 | 1 |
| PURZ 1702 | 0 | 2 | 1 | 0 | 0 |
| XZ14055 | 7 | 5 | 1 | 0 | X |
| XZ14069 | 6 | 10 | 4 | 5 | 4 |
| XZ14070 | 3 | 8 | 1 | 1 | 0 |
| XZ14071 | 5 | 7 | 1 | 0 | 2 |
| XZ14072 | 4 | 7 | 1 | 0 | 1 |
| XZ14074 | 0 | 0 | 2 | 3 | 4 |
| XZ14092 | 1 | 1 | 1 | 1 | 0 |
| ZG09004 | 6 | 4 | 0 | 0 | 0 |
| ZG09055 | 5 | 3 | 0 | X | 0 |
| ZG09062 | 4 | 4 | 3 | 2 | 2 |
| 09-TZ-54-9 | 4 | 7 | 4 | 5 | 4 |
| 09-TZ-89-73 | 1 | 2 | 3 | 0 | 2 |
| 10-TZ-994 | 10 | 4 | 1 | 0 | 0 |
| 10-TZ-1254 | 7 | 9 | 2 | 1 | 3 |
| 15-TZ-11766 | 0 | 4 | 5 | 0 | 3 |
| 16-TZ-12036 | 1 | 4 | 3 | 0 | 1 |
| 16-TZ-12783 | 0 | 8 | 7 | 3 | 2 |
| 16-TZ-13463 | 0 | 2 | 4 | 5 | 2 |
| 16-TZ-14114 | 3 | 6 | 1 | 0 | 0 |
| Chisholm | 3 | 3 | 1 | 1 | 2 |
| Meyer | 7 | 5 | 1 | 0 | 0 |
| Empire | 7 | 4 | 2 | 1 | 0 |
| Jamur | 7 | 4 | 2 | 0 | 2 |
| Zenith | 0 | 3 | 0 | 0 | 2 |
| Riviera | 7 | 0 | 0 | X | 1 |